US009028754B2

(12) United States Patent
Winter et al.

(10) Patent No.: US 9,028,754 B2
(45) Date of Patent: May 12, 2015

(54) RACK ROBOT

(71) Applicant: Hamilton Storage Technologies, Inc., Hopkinton, MA (US)

(72) Inventors: Fabian Winter, Waltham, MA (US);
Halvard Solberg, Merrimack, NH (US);
Julian Warhurst, Ashland, MA (US);
Frank Hunt, Shrewsbury, MA (US);
Behrouz Zandi, Lexington, MA (US)

(73) Assignee: Hamilton Storage Technologies, Inc., Hamilton, MA (US)

( * ) Notice: Subject to any disclaimer, the term of this patent is extended or adjusted under 35 U.S.C. 154(b) by 178 days.

(21) Appl. No.: 13/622,461

(22) Filed: Sep. 19, 2012

(65) Prior Publication Data
US 2013/0151004 A1   Jun. 13, 2013

Related U.S. Application Data

(60) Provisional application No. 61/568,885, filed on Dec. 9, 2011.

(51) Int. Cl.
| G06F 7/00 | (2006.01) |
| G01N 21/00 | (2006.01) |
| G01N 31/00 | (2006.01) |
| G01N 33/00 | (2006.01) |
| G01N 35/00 | (2006.01) |
| G01N 1/42 | (2006.01) |
| B01L 9/00 | (2006.01) |

(52) U.S. Cl.
CPC .............. *G01N 35/0099* (2013.01); *G01N 1/42* (2013.01); *G01N 2035/00435* (2013.01)

(58) Field of Classification Search
CPC combination set(s) only.
See application file for complete search history.

(56) References Cited

U.S. PATENT DOCUMENTS

| 2005/0188705 A1 | 9/2005 | Jones et al. |
| 2007/0258858 A1 | 11/2007 | Rasnow et al. |
| 2010/0066109 A1 | 3/2010 | Pedrazzini |
| 2012/0060514 A1 | 3/2012 | Warhurst et al. |
| 2012/0060520 A1 | 3/2012 | Collins et al. |
| 2012/0060539 A1 | 3/2012 | Hunt et al. |
| 2012/0060541 A1 | 3/2012 | Hunt et al. |

OTHER PUBLICATIONS

International Preliminary Report on Patentability, PCT/US2012/058224, dated of mailing Jun. 19, 2014.
International Search Report and Written Opinion, PCT/US2012/058224, date of mailing Jan. 30, 2013.

*Primary Examiner* — Jill Warden
*Assistant Examiner* — Julie Tavares
(74) *Attorney, Agent, or Firm* — Andrus Intellectual Property Law, LLP

(57) ABSTRACT

A rack robot lifts and transfers sample tube storage racks or plates with a refrigerated enclosure maintained, e.g., at −20° C. The samples are normally held in ultra-low temperature, e.g., −80° C., or cryogenic freezers. From time to time, the racks or plates need to be roved from the ultra-low temperature or cryogenic freezers for processing and the rack robot transfers the racks or plates to the various processing stations within the refrigerated enclosure, such as tube picking, barcode reading, or frost removal stations.

9 Claims, 16 Drawing Sheets

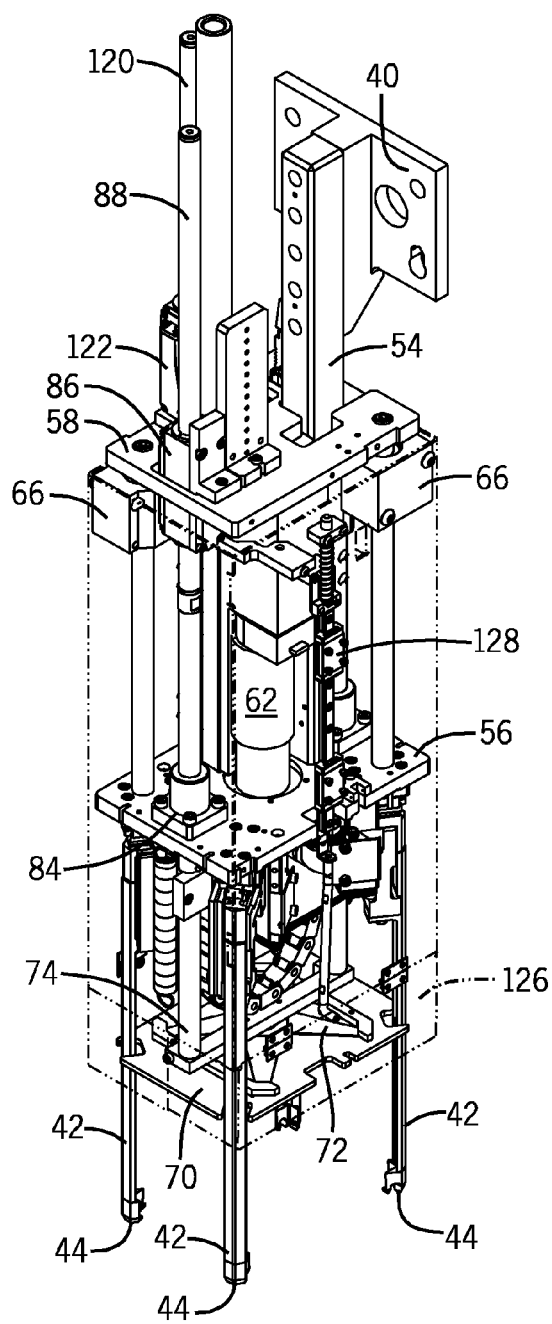
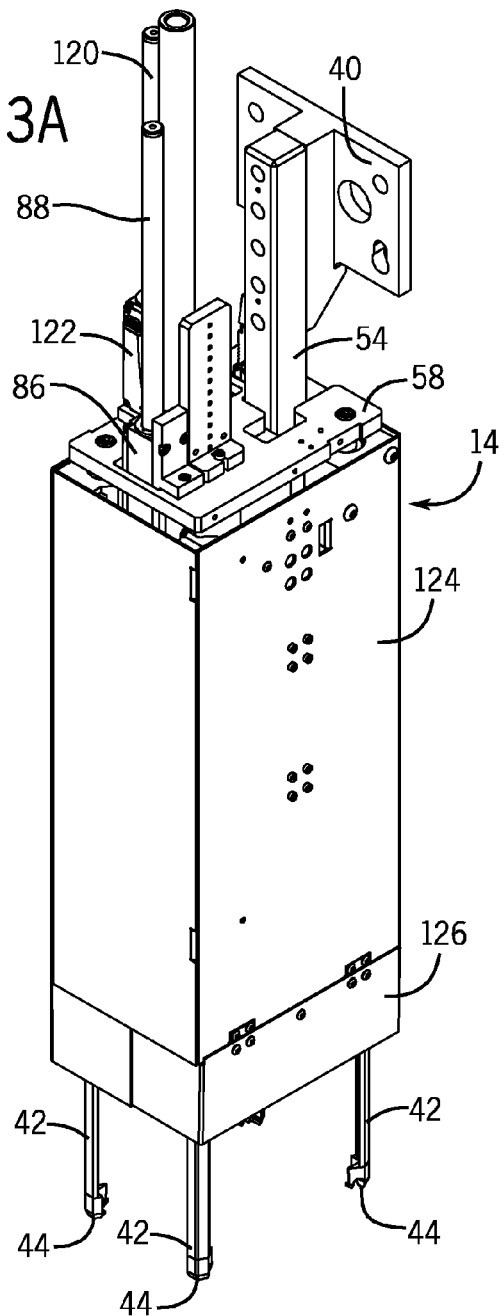

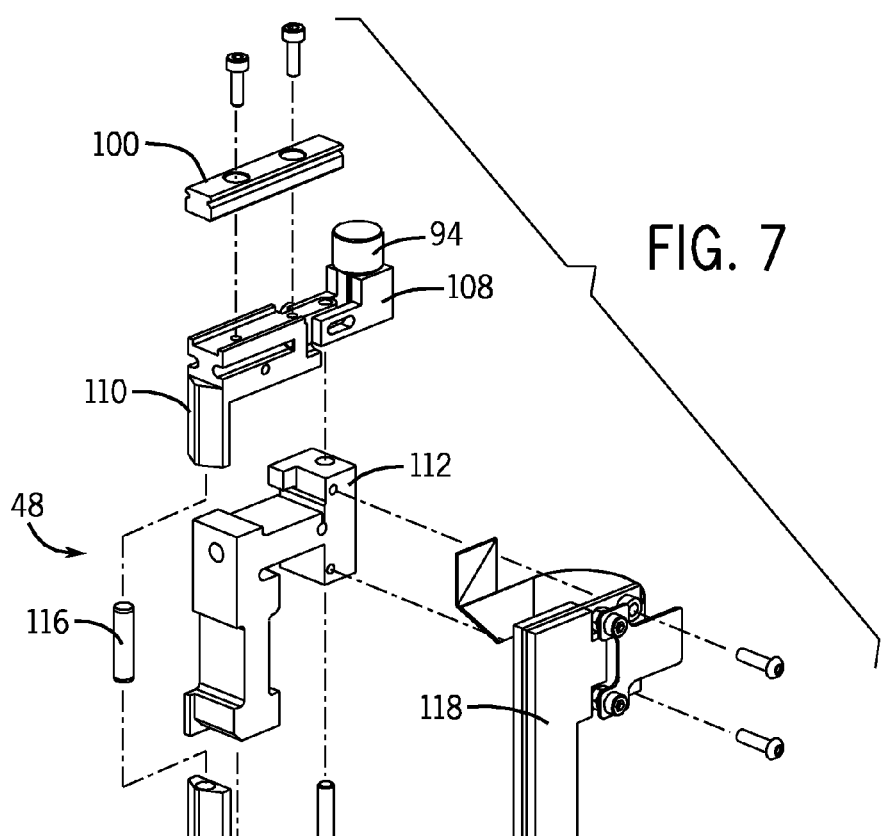
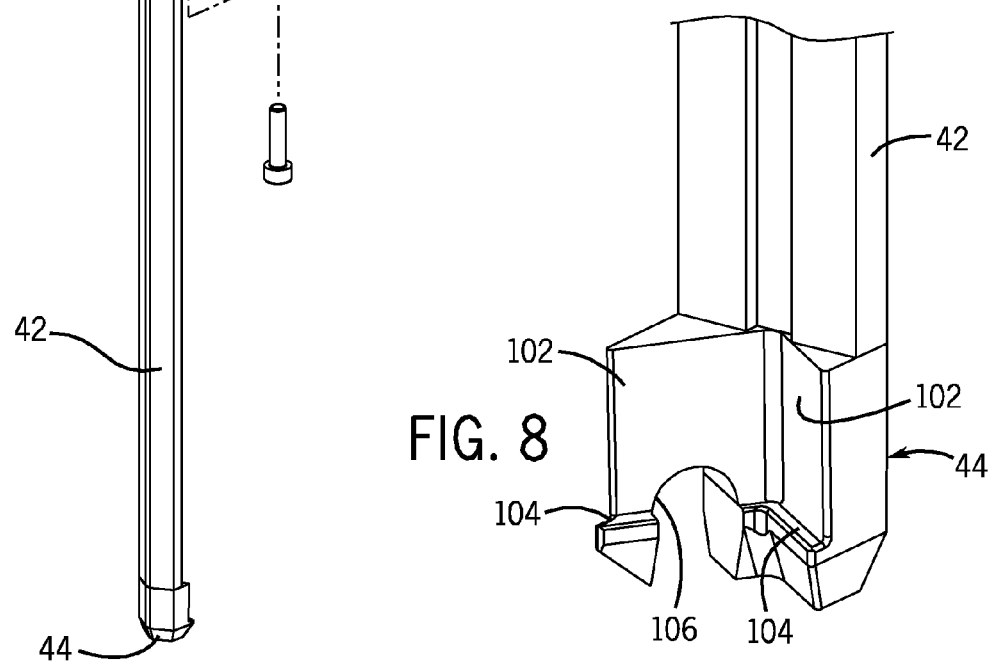
FIG. 7
FIG. 8

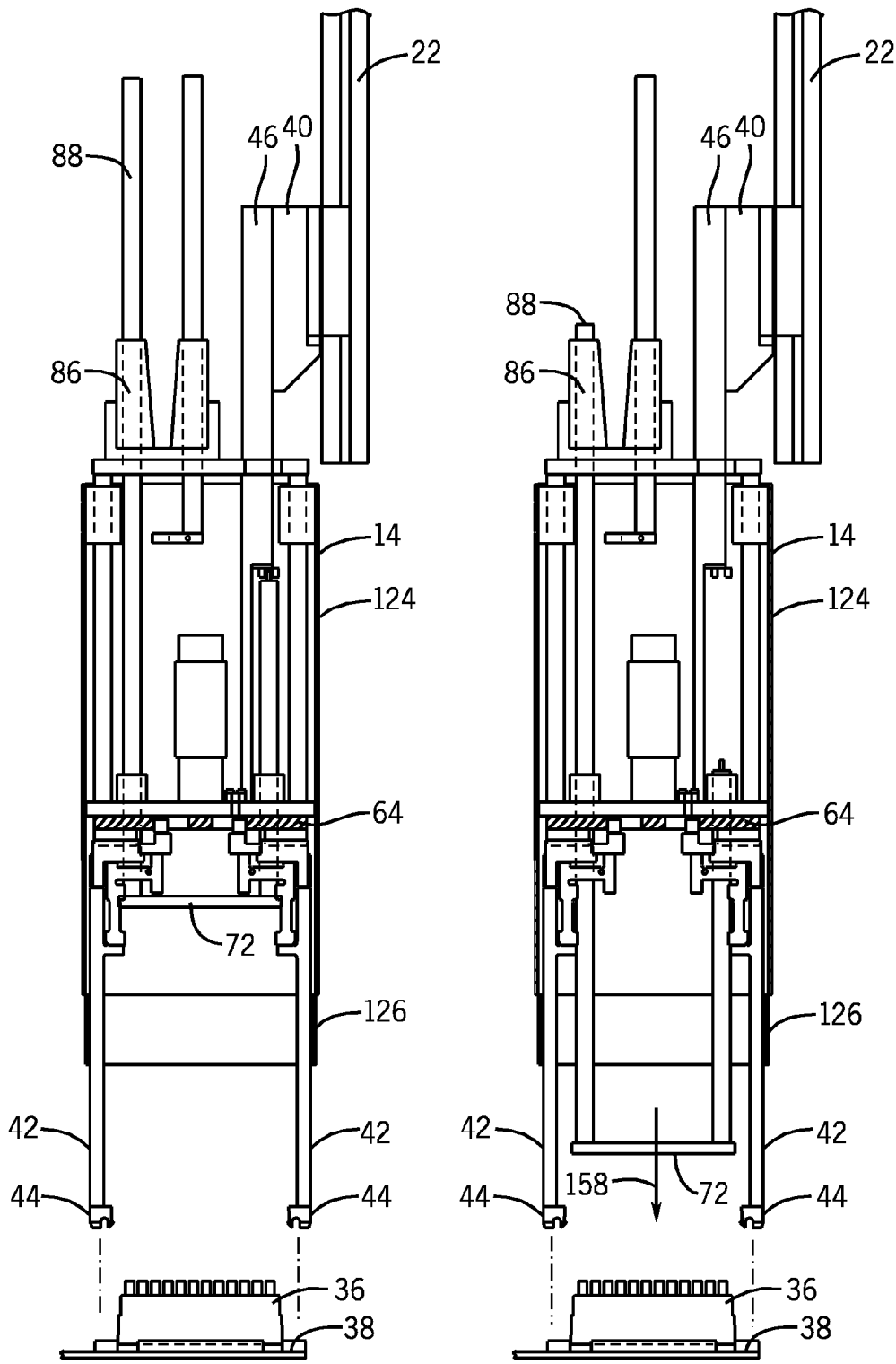

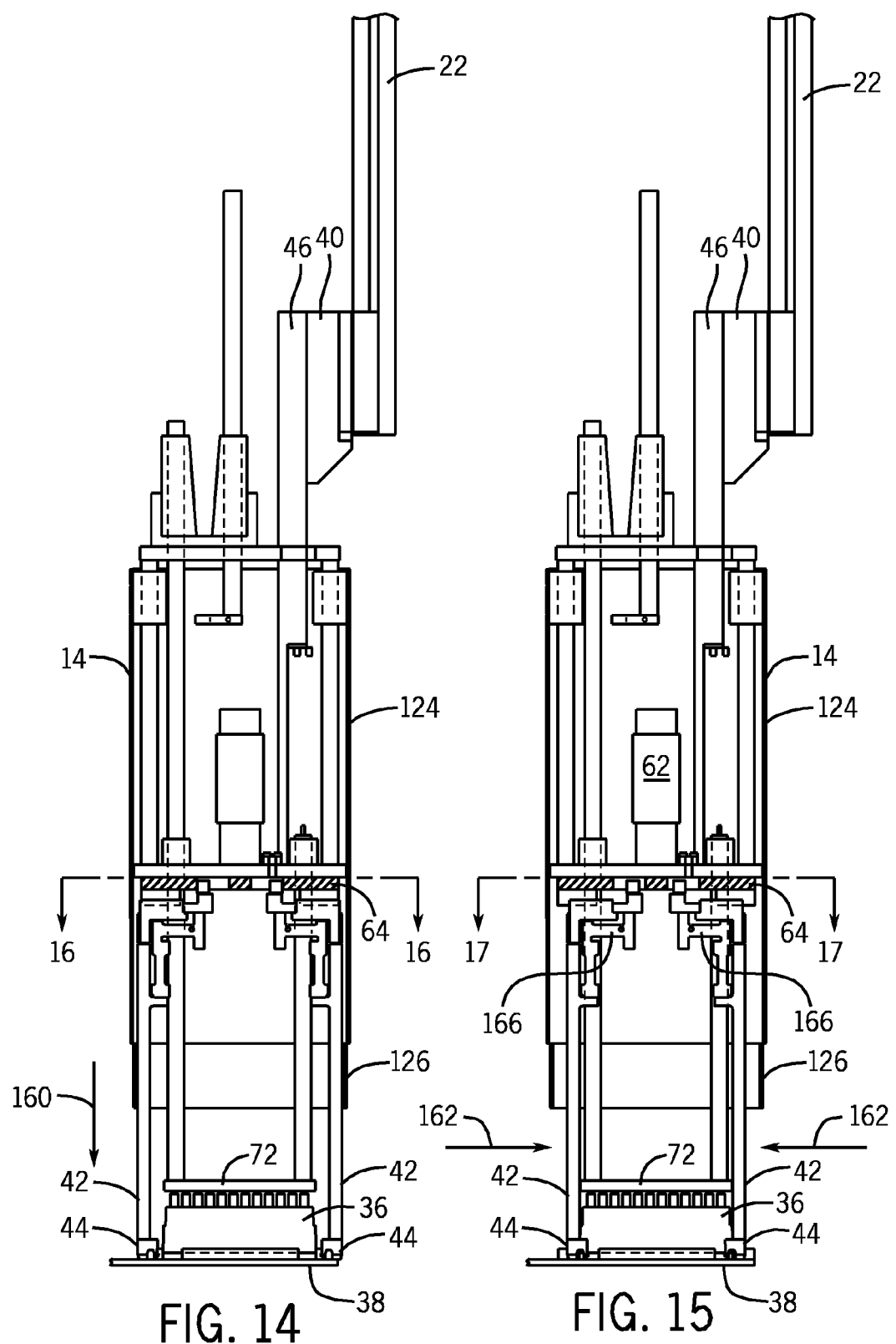

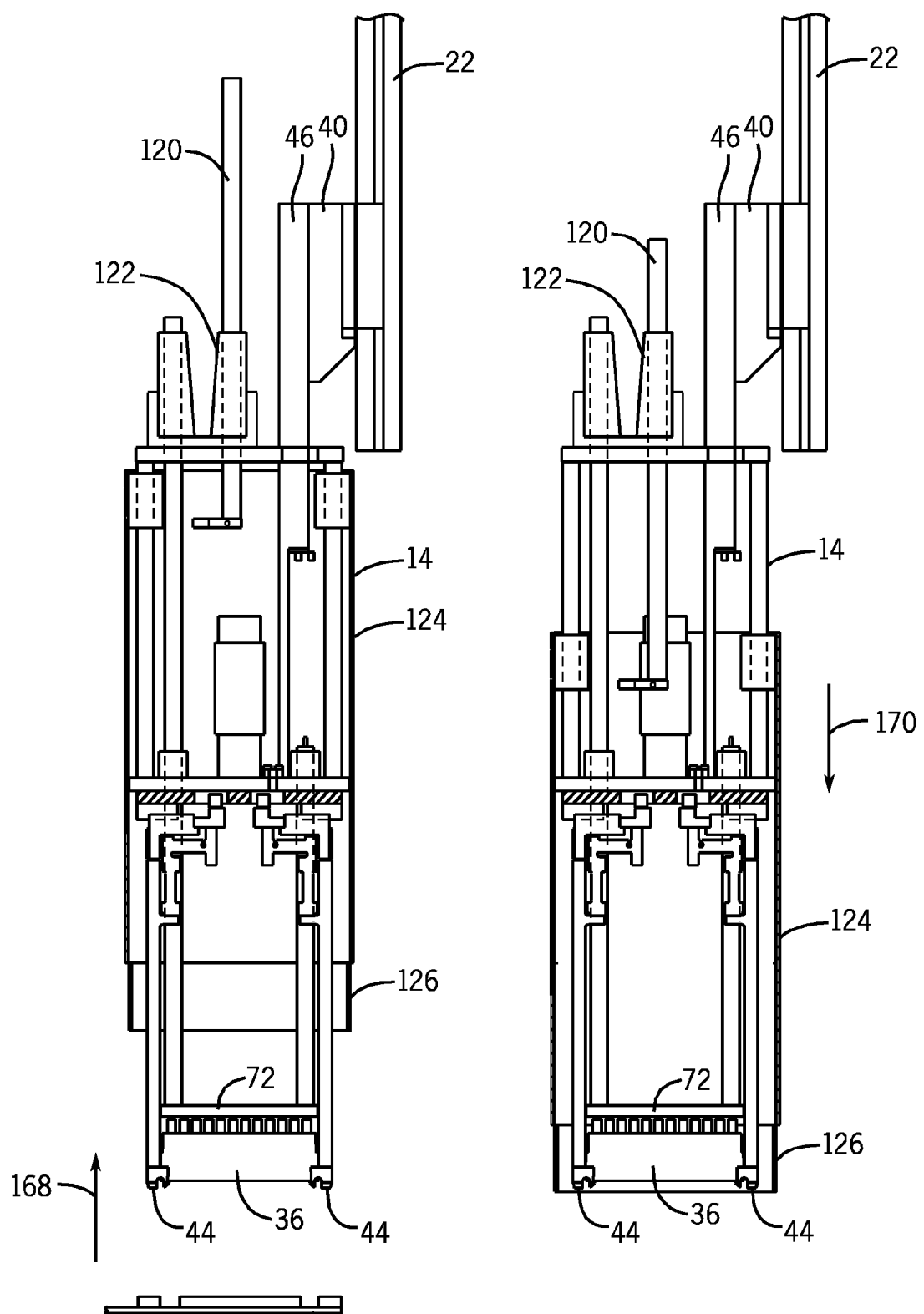

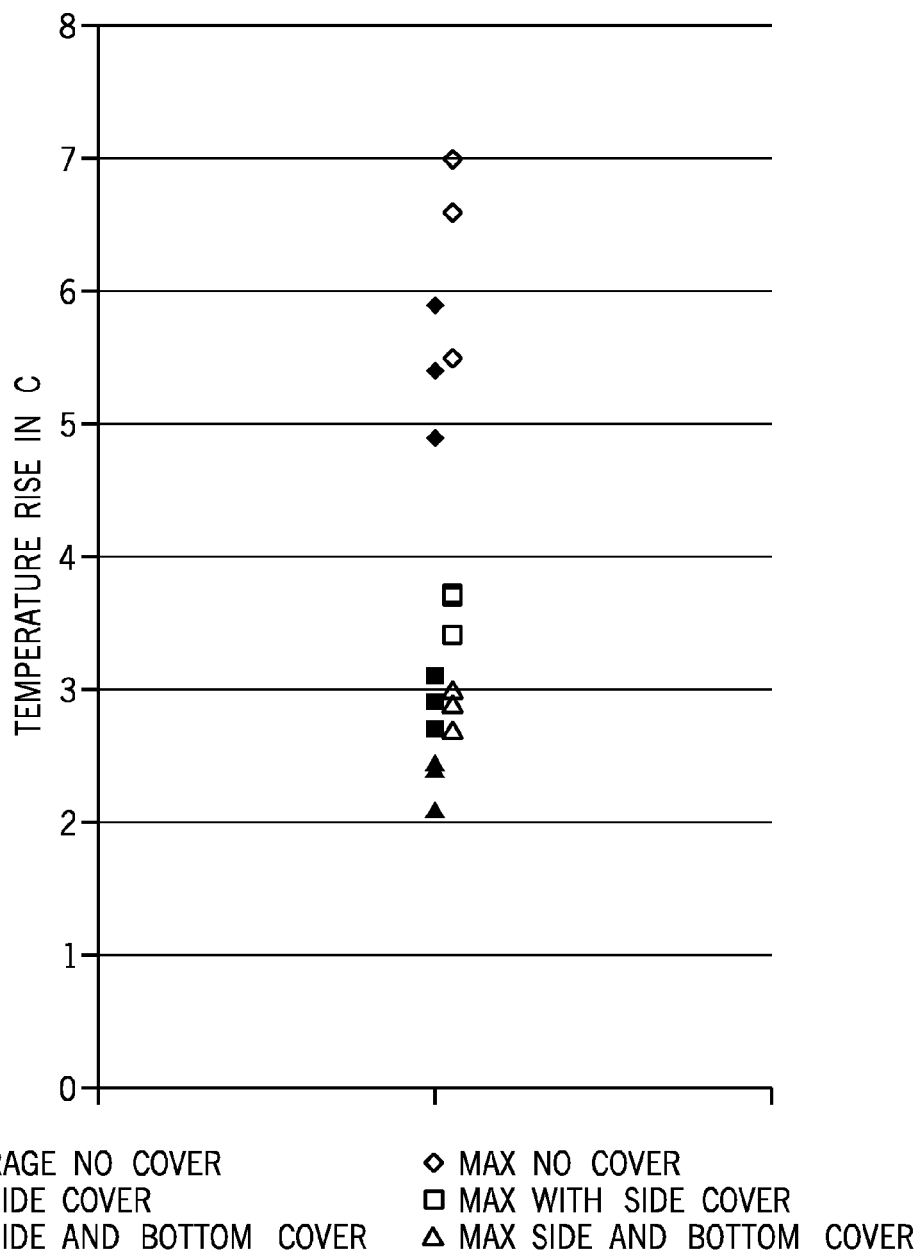

RACK ROBOT

FIELD OF THE INVENTION

The invention relates to automated storage and retrieval systems for ultra-low temperature or cryogenic freezer systems used primarily to store biological or chemical samples. In particular, the present invention pertains to a rack robot that transports sample tube storage racks or sample storage plates within the system for processing when the tube racks or plates are removed from ultra-low temperature or cryogenic freezers in which the racks or plates are normally placed for storage.

BACKGROUND OF THE INVENTION

Storage of biological and chemical samples is becoming widespread in the biotechnology and medical industries. To preserve many of these samples, the samples must be stored well below normal freezing temperatures. Generally speaking, a regular freezer operates from −5° C. to −20° C., an ultra-low temperature freezer operates from about −50° C. to −130° C. (preferably at about −80° C.) and a cryogenic freezer operates from about −140° C. to −196° C. (the boiling point of liquid nitrogen). The present invention is directed to a large automated storage and retrieval system containing one or more ultra-low temperature or cryogenic freezer bays operating below about −65° C. The freezers are contained within a refrigerated enclosure, preferably maintained at about −20° C.

Most biological samples stored in ultra-low temperature or cryogenic systems are contained in sealed plastic laboratory tubes held in tube storage racks in arrays of, for example, 48, 96 or 384 tubes. In some cases, a two dimensional barcode is adhered to the bottom of the tubes and is able to be read through the bottom of the storage racks. In other cases, a one dimensional barcode is placed on the side of the wall of the tube. It is also typical for the sample storage racks themselves to have a barcode. In all cases, bar coding facilitates data entry into a control system that keeps track of the location of each of the biological samples. In some applications, samples are stored in sample storage plates such as sealed microtitre plates or wellplates, rather than stored in sealed tubes held in a rack.

In the art, it is known to store tube storage racks or plates on vertical shelves in cassettes or in drawers in ultra-low temperature or cryogenic freezer chests, which in turn are located within a refrigerated (e.g., −20° C.) work space. In these systems, active robotic equipment operates in the −20° C. environment to pull the tube storage racks or plates from the ultra-low temperature or cryogenic freezer(s) for sample retrieval and placement. The present invention is directed primarily to an automated rack robot for transporting sample storage tube racks or plates in the −20° C. environment within the system after the cassette of racks or plates has been pulled from a bank of ultra-low temperature or cryogenic freezer chests. The preferred cassette puller is designed according to U.S. patent application Ser. No. 13/228,651, entitled "Cassette Puller", Publication No. US2012/0060539A1 (now abandoned) filed on Sep. 9, 2011, and incorporated herein by reference, and is also designed to accommodate storage cassettes as described in co-pending U.S. patent application Ser. No. 13/228,662, entitled "Sample Storage Cassette for Ultra-Low or Cryogenic Temperatures", Publication No. US2012/0060541A1 filed on Sep. 9, 2011, also incorporated herein by reference. The preferred cassette puller includes an insulated sleeve into which a cassette is pulled from the freezer and then ejects a selected tube storage rack or plate onto an ejector plate or onto an alternative staging area outside of the sleeve to present the rack or plate within the −20° C. environment for processing.

One of the primary purposes of the rack robot is to reliably lift and transfer tube storage racks or plates within the warmer −20° C. environment for processing, e.g. from the cassette puller to a tube picking station, a barcode reading station, a frost removal station, or other location, or for returning the rack or plate to the ultra-low temperature or cryogenic freezer. For example, placement of racks or plates, or tubes within tube racks may not be as expected or precise for a number of reasons such as frost accumulation or other physical contingencies. In this regard, an objective of the invention is to ensure that tubes are in place in racks and that racks or plates are secure prior to lifting and transfer with the rack robot. In addition, it has been found that the speed at which the rack robot operates is often a throughput bottleneck and slows overall operation of the system. Therefore, another objective of the invention is to minimize the time necessary to reliably lift and transfer plates or racks. Further, another objective of the present invention is to limit undesirable sample temperature rise when transferring samples within the warmer −20° C. environment, which is, e.g., about 60° C. warmer than the freezer temperature in a system with ultra-low temperature (−80° C.) freezers.

SUMMARY OF THE INVENTION

The invention pertains to a rack robot for use in an automated storage and retrieval system, and includes various features that enable the rack robot to accomplish the above described objectives. As mentioned, the primary purpose of the rack robot is to lift and transfer sample tube storage racks or plates automatically within a refrigerated enclosure maintained at a low temperature of approximately −15° C. to −30° C. The overall system in which the rack robot would normally be used further includes one or more freezers maintained at or below −65° C. into which sample tube storage racks or plates are normally held for long term storage. Once the sample tube storage racks or plates are pulled from the freezers maintained at or below −65° C. and presented within the low temperature environment of approximately −15° C. to −30° C. inside the refrigerated enclosure, the rack robot is designed to lift and transfer the racks or plates within the low temperature environment for processing by other equipment located within the refrigerated enclosure such as tube picking stations, barcode readers, frost removal stations or other processing equipment that may be desirable to locate within the refrigerated enclosure. In the preferred embodiment of the invention, the horizontal and vertical movement of the rack robot through the low temperature environment within the refrigerated enclosure is controlled by a gantry robot. Thus, in the preferred embodiment of the invention, actuating motors on the rack robot operate to lift a selected sample tube storage rack or plate in a prompt and reliable fashion, and the system relies on the operation of the gantry robot to move the rack robot and the lifted sample tube storage rack or plate throughout the refrigerated enclosure in horizontal and vertical directions to the various processing stations. Those skilled in the art should appreciate that various aspects and features of the rack robot can be implemented in systems in which the horizontal and vertical movement of the robot is not controlled by a separate gantry robot. In addition, those skilled in the art will understand that while the features of the rack robot are particularly useful for transporting racks or plates through a low temperature environment within a refrigerated enclosure, aspects of the rack robot may be used in other applications as well.

In accordance with one aspect of the invention, the rack robot includes a base from which four legs with lifting feet at their bottom end extend downwardly. Each of the lifting feet is adapted to lift a selected corner of a sample tube rack or plate. The rack robot moves the lifting feet toward one another to position the lifting feet for lifting a rack or plate from a first location or apart from one another to release and set the tube rack or plate at the same or second location. In practice, the legs and lifting feet are spread apart and the rack robot is lowered to lower the feet to the appropriate height around the sample tube rack or plate intended to be lifted. The rack robot includes an actuating motor and a cam mechanism that simultaneously moves the lifting feet toward one another to position the lifting feet at and underneath a respective corner of the tube rack or plate prior to lifting the tube rack or plate. Once the legs and feet are properly positioned, the rack robot including the base, the actuating motor, the cam mechanism, the downwardly extending legs and feet are lifted, for example by a gantry robot, and transferred vertically and/or horizontally to a location at which it is desired to place the tube rack or plate. The actuating motor and cam mechanism then simultaneously moves the lifting feet apart from one another to release and set the tube rack or plate at the desired location. It should be noted that the lifting legs may often extend downward into environments held at ultra-low (e.g., −80° C.) or cryogenic temperatures. Thus, it is desirable that the actuating motor and other electronic components be located at the upper end of the rack robot which remains in the low temperature (e.g., −20° C.) environment.

It is preferred that the lifting feet lift the tube rack or plate at the corners so that substantial portions of the tube rack or plate being lifted are visually exposed. This will enable the rack robot to transfer the tube rack or plate to a barcode reading station and enable a barcode presented on a sidewall of the tube rack or plate to be read at the barcode reading station without releasing the plate or rack and removing the robot from the vicinity of the plate or rack during the barcode reading process. It is also desirable that the bottom of the tube racks be left visually exposed to enable reading of barcodes on the bottom of storage tubes held in racks without the need to release the rack. Further, it is desirable that each of the lifting feet at the corners include an opening that provides visual clearance to view a corner portion of the sidewall of a lifted sample tube rack or plate in order to allow an optical sensor to determine whether the A1 notch on the sample tube rack or plate is present at the respective corner in order to determine the orientation of the rack or plate. In the preferred embodiment of the invention, each lifting foot includes an upstanding wall shaped to extend around the corner of the sample tube storage rack or plate that is being lifted and also includes a horizontal step extending inward from the upstanding sidewall that is also shaped to extend around the corner. It is desirable that the bottom of the tube rack or plate be lifted by the horizontal steps on the respective feet, so that horizontal pressure applied by the feet against a sample tube storage rack or plate can be minimized. At ultra-low temperatures, it is typical for the sample tube storage rack or plate to become brittle and therefore minimizing horizontal gripping forces of the lifting feet facilitates long term reliability of the system and lessens damage of the sample tube racks or plates.

It is preferred that the rack robot include deflection sensors associated with the horizontal movement of each leg and lifting foot. The deflection sensors output signals that are used by the system control to detect the presence of the tube rack or plate between the lifting feet prior to lifting. The deflection signals are also preferably used by the system control for crash detection, automatic identification of precise physical position of racks or plates, for controlling the horizontal closing force of the feet, and also for monitoring the quality at which the feet have gripped the sample tube rack or plate prior to lifting. In operation, it is desired that the rack robot be located directly above the lifting location such that the geometric center of the rack or plate aligns precisely with the central axis of the robot between the lifting feet. However, in practice, the location of the sample tube rack or plate is often somewhat misaligned. In the preferred embodiment, the system accounts for such misalignment prior to closing the lifting feet using the signals from the deflection sensors associated with the horizontal movement and force of each leg. In other words, the system can be designed to adjust the horizontal X-Y position of the rack robot and the legs and lifting feet so that the amount of force and/or deflection imparted to each of the four respective legs are more balanced with one another.

The preferred embodiment of the invention also includes deflection sensors associated with the vertical movement of each of the legs. These sensors are primarily used to teach the system height requirements to which the lifting feet need to be placed at various locations within the refrigerated enclosure, and also to determine whether the lifting feet have encountered an unexpected obstacle when being lowered during system operation. Signals from the vertical deflection sensors for the legs and lifting fingers can also be used to decelerate movement in case vertical deflection is detected, or check whether the horizontal position of the fingers are appropriate prior to lifting and transfer.

In another aspect of the invention, the rack robot includes a vertically repositionable lid that is capable of being positioned above a storage tube rack or plate held within closed lifting fingers. One purpose of the repositionable lid is to ensure the security of tubes in the tube rack when the tube rack is lifted and transferred to another position. It is desirable that the relative height of the lid with respect to the lifting feet be adjustable so that the robot can be used to transfer racks having tubes of different height. The lid should hover slightly above the height of the tubes when the tubes are fully seated within the tube rack such that the lid does not touch the top of the tubes during normal operation. It is further desired in the preferred embodiment of the invention that an acceleration sensor or sensing system sense the acceleration of the repositionable lid. The system control uses the signal from the acceleration sensor to detect whether one or more sample tubes or tube caps are not properly seated within the tube rack prior to lifting the tube. If the system detects that a sample tube or cap is ajar, the system control in response to the signal from the acceleration sensor can decelerate the movement of the lid with limited applied force in order to reseat the sample tube or cap within the tube rack. The lid acceleration sensor can also be used to identify labware height.

In another aspect of the invention, the rack robot includes a tubular sidewall cover surrounding the downwardly extending legs. The purpose of the cover is to reduce temperature rise of the samples being transferred within the refrigerated environment (e.g. −20° C.) when the samples have been pulled from the ultra-low temperature (e.g. −80° C.) or cryogenic freezer banks. The cover is desirably repositionable with respect to the rack robot base, legs and lifting fingers. The cover can be positioned at a height above the lifting feet to enable the lifting legs and fingers to penetrate downward beyond the height of the cover, e.g. when it is necessary to do so in order to lift a storage tube rack or plate from a tight location in which the cover will not fit, or to allow visual access for rack inspection from the side with a camera when gripping the rack. In some applications, it may be desirable to further include one or more bottom doors that close underneath the lifting feet after the rack robot has been lifted to lift a tube storage rack or plate from a given location. In this arrangement, it is desirable that the one or more doors be mechanically coupled to the tubular sidewall cover so that the one or more doors close automatically when the rack robot is raised vertically.

Those of ordinary skill in the art should appreciate that it is not necessary that the rack robot include all of the features described above, and further that a rack robot constructed in accordance with the invention is capable of achieving the objectives identified above. Other aspects, features and advantages of the invention will be apparent to those skilled in the art upon reviewing the drawings and following description thereof.

BRIEF DESCRIPTION OF THE DRAWINGS

FIGS. 3A and 3B are detailed perspective views of a rack robot constructed in accordance with a preferred embodiment of the invention.

FIG. 7 is a detailed view of the components of the lifting legs including a mounting block for horizontal and vertical deflection sensors.

FIG. 8 is a detailed view of the preferred configuration for the lifting feet.

FIGS. 12-15 are schematic drawings illustrating the lifting of a sample tube rack using the rack robot.

FIG. 18 is a schematic view illustrating the rack robot lifting the tube storage rack from a first location.

FIG. 19 is a schematic view illustrating the rack robot preparing to lower the sample tube rack at a second location.

FIG. 21 is a plot containing data relating to a sample temperature rise experiment.

DETAILED DESCRIPTION

Figure 1:
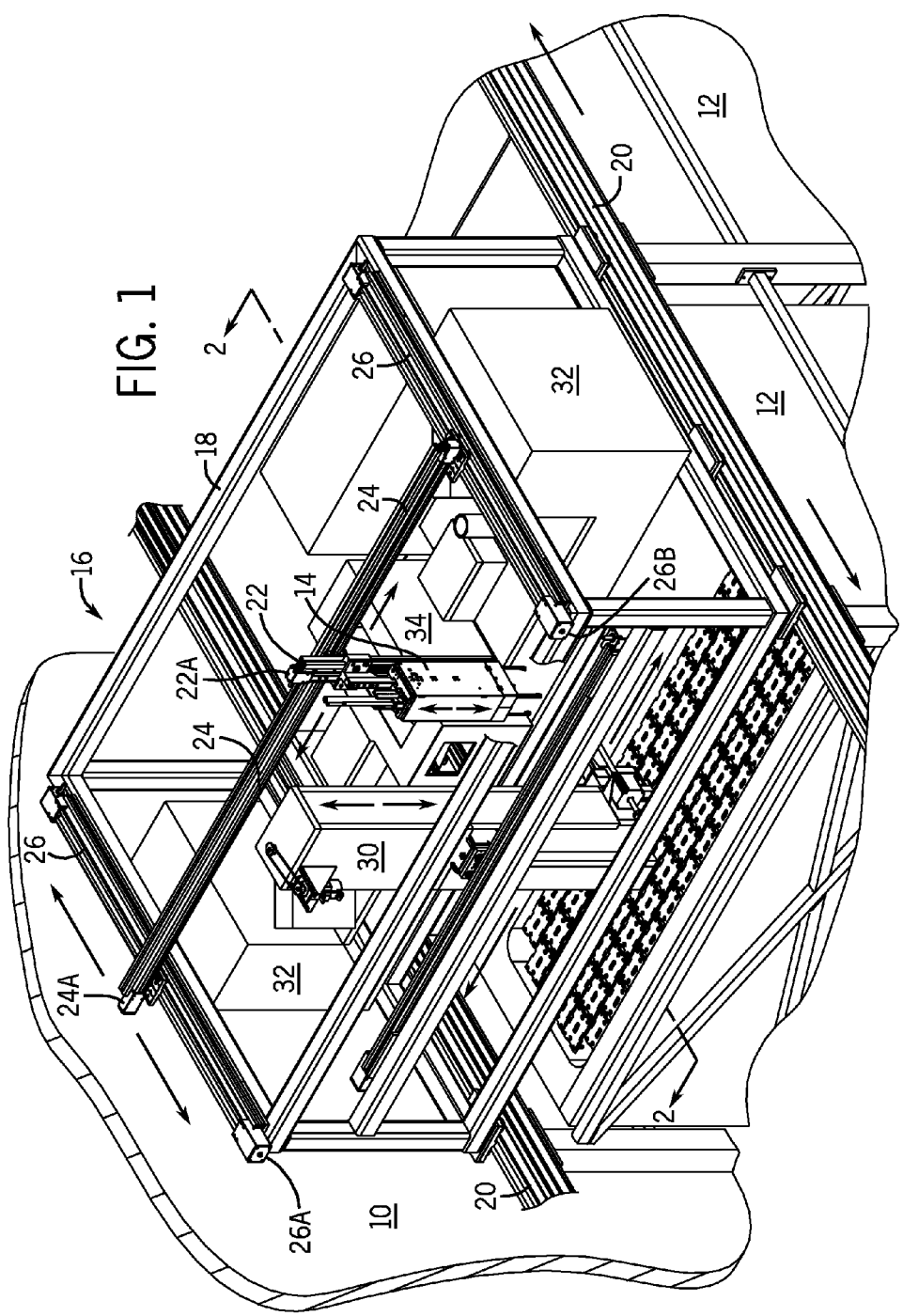
FIG. 1 is a perspective view of a rack robot constructed in accordance with a preferred embodiment of the invention mounted to a traveling gantry along with other components such as a cassette puller, tube picking mechanisms and a barcode reader. The traveling gantry is located within a refrigerated enclosure maintained for example at −20° C.

Referring to FIG. 1, an automated storage and retrieval system 16 constructed in accordance with the preferred embodiment of the invention includes a number of components mounted to a gantry 18. The gantry 18 travels throughout a refrigerated enclosure 10 generally for the purpose of parking a cassette puller 30 in an appropriate position over a bay in a freezer chest 12 to access a cassette in the freezer 12 containing sample tube storage racks or plates or over an input/output module for the refrigerated enclosure to access cassettes in the input/output module. The refrigerated enclosure 10 is maintained at a temperature of approximately −15° C. to −30° C., preferably about −20° C., as is described in the above incorporated Patent Application entitled "Cassette Puller", application Ser. No. 13/228,651 (now abandoned).

In the preferred application of the invention, multiple horizontal freezer chests 12 are located within the refrigerated enclosure 10. Each freezer 12 includes a storage compartment or freezer bay maintained at or below −65° C. under normal operating conditions. Preferably, each freezer chest 12 includes two independently cooled bays. Biological or chemical samples stored in sealed storage tubes held in tube racks or stored in sealed well plates are stored within the freezer chest 12. In an ultra-low temperature system, the temperature within the freezer chest 12 will be maintained at for example −80° C. In a cryogenic system, the temperature within the chest 12 ma be maintained at a temperature as low as −196° C. The refrigerated enclosure 10 provides a low temperature (−15° C. to −30° C., e.g. −20° C.) work space for an automated storage and retrieval system 16. The automated storage and retrieval system 16 in general is mounted to a traveling gantry 18 that is driven linearly along horizontal Y-axis drive rails 20. The gantry 18 moves over and above the top of the freezer chest 12 and also over the input/output modules, and thus as mentioned provides the automated storage and retrieval system 16 with access to storage cassettes and/or input cassettes stored in the freezers 12 and input/output cassettes residing in the input/output modules. The invention is not limited to the specific configuration of the freezer chest, cassette puller or the input/output modules. Nevertheless, it is preferred that the input/output cassettes of input/output modules be constructed in accordance with the description in U.S. patent application Ser. No. 13/229,075, entitled "Input/Output Module and Overall Temperature Controlled Samples", Publication No. US2012/0060520A1 (now abandoned) filed on Sep. 9, 2011 and incorporated herein by reference.

Referring still to FIG. 1, a rack robot 14 constructed in accordance with a preferred embodiment of the invention is mounted to the gantry via Z-axis indexing drive rail 22, X-axis indexing drive rail 24, and Y-axis indexing drive rail 26. Once the gantry 18 is stationed in the desired Y-axis position within the refrigerated enclosure by movement along Y-axis drive rails 20, indexing drives position the rack robot 14. Indexing drive motor 22A is controlled to reposition the rack robot 14 along the Z-axis indexing drive rail 22. Indexing drive motor 24B is controlled to reposition the rack robot 14 in the X direction along the X axis indexing drive rail 24, and indexing drives 26B are controlled to reposition the rack robot 14 in the Y axis relative to the position of the gantry 18. Thus, the vertical and horizontal movement of the rack robot 14 is controlled by motion along the indexing rails 22, 24 and 26 mounted on the gantry. It should be noted that the invention is not limited to the particular configuration of the indexing drive on the gantry 18 shown in FIG. 1.

Other components shown to be mounted to the gantry 18 include a cassette puller 30, and a first and second tube picking station 32, and a barcode reader 34. The preferred configuration of the tube picking mechanism 32 is described in U.S. patent application Ser. No. 13/193,838, entitled "Tube Picking Mechanisms With an Ultra-Low Temperature or Cryogenic Picking Compartment", Publication No. US2012/0060514A1 filed on Jul. 29, 2011, the disclosure which is herein incorporated by reference. Other components such as a frost removal station or additional barcode readers or other desirable components can be mounted to the gantry 18. The purpose of the rack robot 14, as mentioned, is to lift and transfer sample tube storage racks through the low temperature environment (about −20° C.) between the various components mounted on the gantry 18. The processing bottle neck in the system tends to be the transporting of tube storage racks or plates between the various components on the gantry and therefore as mentioned prompt, reliable transportation is important. If desirable, the system can include a second rack robot mounted to the gantry, for example, by mounting a second Z-axis indexing drive rail and rack robot to the X-axis indexing drive rail 24. It is also important to note that the samples maintained at an ultra-low or cryogenic, temperature (e.g. less than −65° C., preferably −80° C. or cryogenic) are substantially colder than the −20° C. environment within the refrigerated enclosure 10. Even a small temperature rise in samples can adversely affect the samples and therefore it is desirable to minimize exposure time within the −20° C. environment. The tube picking mechanisms 32 each include a chamber held at the ultra-low or cryogenic temperature as discussed in the above incorporated patent application. Thus, the rack robot 14 is designed to facilitate fast, reliable transfer from the cassette puller 30 to the tube picking stations 32. In addition, the rack robot 14 includes a cover to reduce temperature rise of the samples during the lifting and transfer process. Further, the rack robot 14 is designed to allow the barcode reader optical access to the locations on tube storage racks or plates where barcodes are normally located, for example a sidewall portion of the plates or racks, or the bottom of sample tube storage racks where 2D barcodes are normally placed on the individual tubes.

Figure 2:
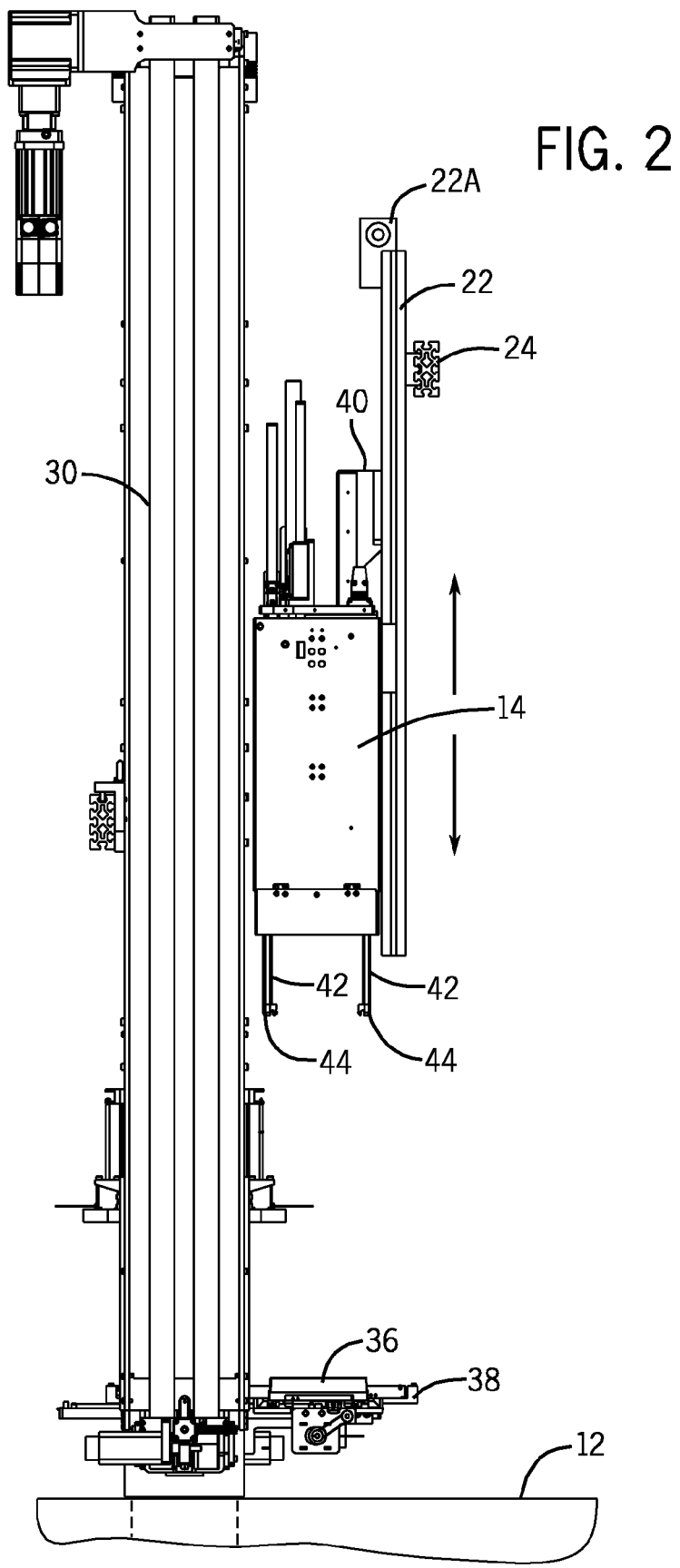
FIG. 2 is a side elevation view taken along line 2-2 in FIG. 1 showing a rack robot constructed in accordance with the preferred embodiment of the invention being positioned adjacent a cassette puller and positioned above a sample tube storage rack that has been presented in the −20° C. environment outside of the ultra-low temperature or cryogenic freezer bank.

Referring to FIG. 2, the rack robot 14 has been positioned by the gantry drive rails 24, 26 to a position adjacent the cassette puller 30. In particular, the rack robot 14 is located above a tube storage rack 36 located on the ejector plate 38 for the cassette puller 30. The rack robot 14 and specifically bracket 40 mounted to a base assembly for the rack robot 14 is mounted to the Z-axis indexing drive rail 22 and is lowered along the Z-axis indexing drive rail 22 in order to position the rack robot 14 to lift the rack 36 from the ejector plate 38. The lifting feet 44 at the bottom of the legs 42 on the rack robot 14 are used to lift the rack 36.

Figure 4:
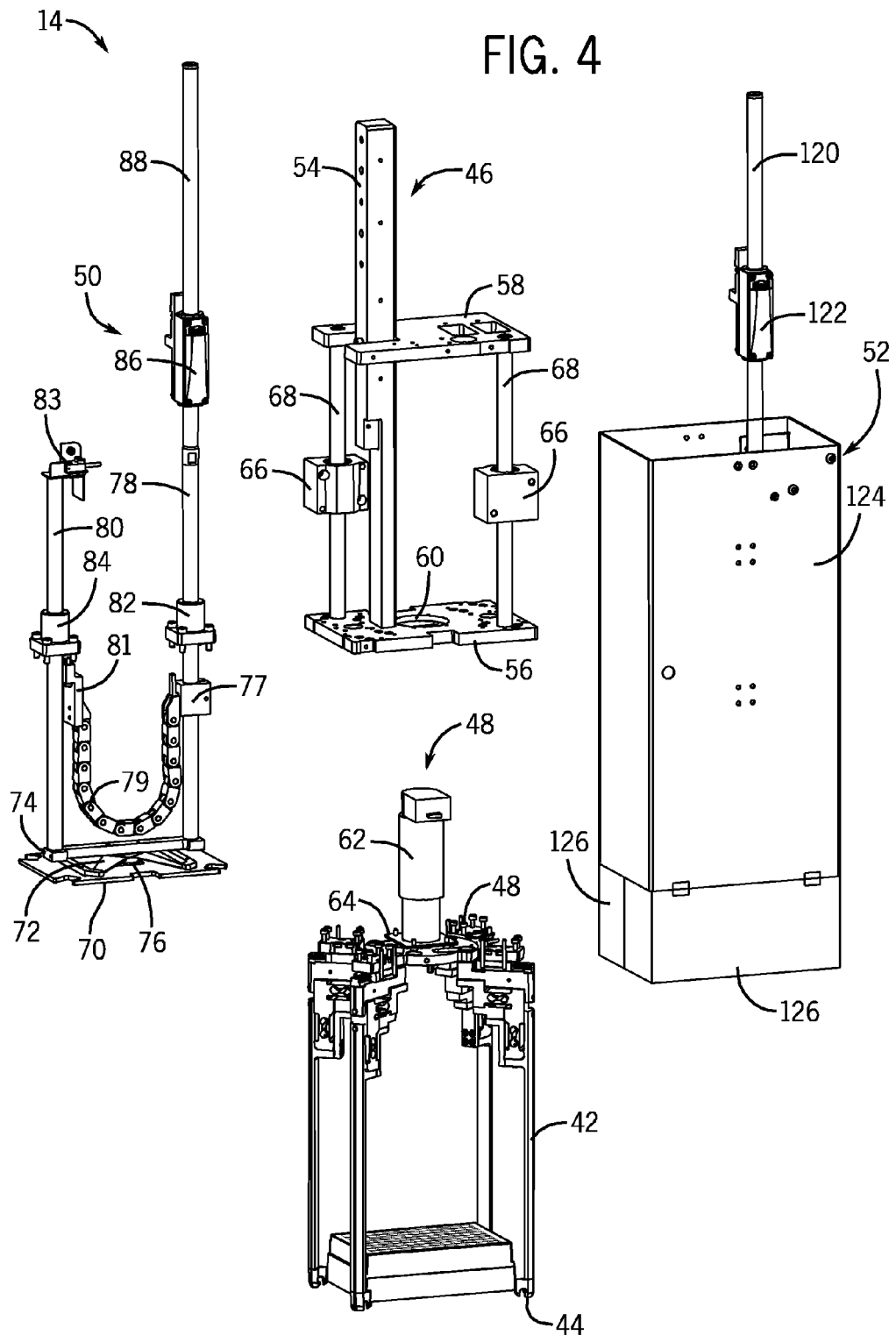
FIG. 4 is an exploded view showing various components of the preferred rack robot, namely a base assembly, a lid assembly, a lifting assembly, and a cover assembly.

Referring now to FIGS. 3A-B and 4, the rack robot 14 includes four major subassemblies which are shown disassembled in FIG. 4 and assembled in FIGS. 3A-B. The four major subassemblies are the base subassembly 46, the lifting assembly 48, a lid subassembly 50 and a cover subassembly 52. The base subassembly 46 includes a main vertical beam 54 that is attached to the bracket 40 (FIGS. 2, 3A, 3B) which is mounted to the Z-axis indexing drive rail 22. The base subassembly 46 also includes a main base plate 56 and a top base plate 58 that are mounted to the beam 54. The main base plate 56 includes an opening 60 to provide clearance for an actuating motor 62 for a cam mechanism 64 on the lifting assembly 48. The base assembly 46 also includes bearing blocks 66 mounted for vertical movement along vertical rods 68 mounted between the base plates 56, 58. The cover 52 is mounted to the bearing blocks 66 and is thus able to be vertically repositioned with respect to the base assembly 46.

Referring still to FIG. 4, the lid assembly 50 includes a plate 70 that is mounted via a spring 72 to a lid support frame 74. An acceleration sensor 76 is located on the top surface of the lid plate 70. Bearing blocks 82, 84 are mounted to the main base plate 56 on the base subassembly 46. Rods 78, 80 are mounted through bearing blocks 82, 84 respectively for vertical movement. A linear drive motor 86 mounted to the upper base plate 58 drives an upper extension 88 of the rod 78 to raise and lower the lid 70. The upper portion of the rod 88 is magnetic and the linear drive 86 drives the magnetic rod 88 in order to move the lid assembly vertically with respect to the base plate 56 and the lifting feet 44. The wiring from the acceleration sensor 76 extends to sensor wiring block 77 which is attached to and moves with the lower rod 78. From the sensor wiring block 77, wiring for the acceleration sensor 76 passes through an e-chain element 79 to a bracket 81. The bracket 81 is mounted to the base plate 56 and does not move with rod 80 on the other side of the lid assembly 50. A proximity or homing sensor 83 is located at the top end of the rod 80.

Figure 6:
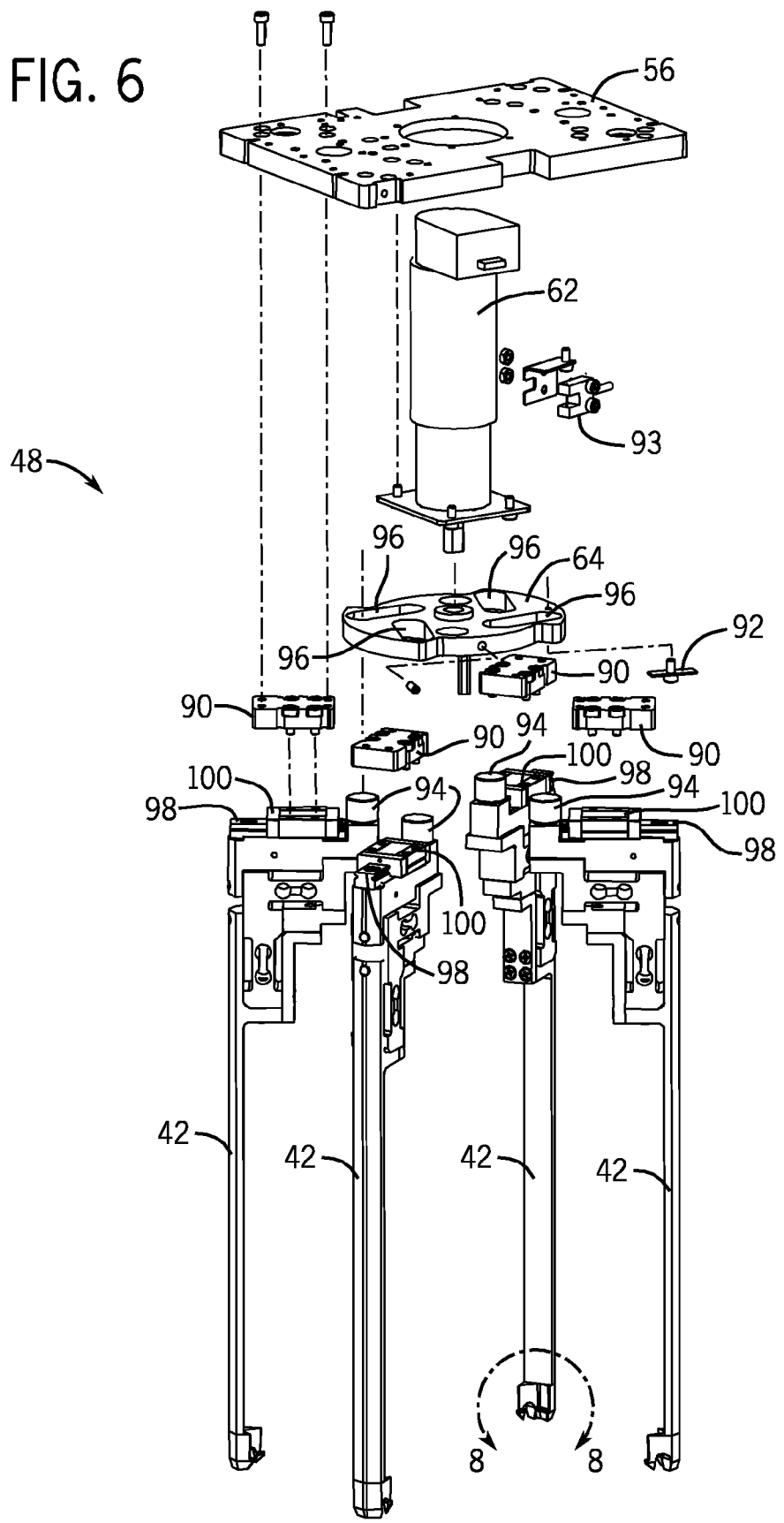
FIG. 6 is a part diagram for the lifting assembly.

Referring now to FIG. 6, the lifting assembly 48 includes a cam actuating motor 62 that is mounted to the main base plate 56 and is operated to turn a slotted cam 64. The top end of each lifting leg 42 includes a cam follower 94 that resides in a respective slot 96 on the cam 64 when the lifting assembly 48 is fully assembled. The upper horizontal surface of the lifting legs 42 also includes a bearing rail 98. A linear bearing 100 is mounted to each respective rail and in turn is mounted through spacer block 90 to the base plate 58. The linear bearings 100 are thus fixed in relation to the base plate 58. As the cam 64 is turned, the cam slots 96 exert force on the cam followers 94 to move the lifting legs 42 inward towards the center of the cam or outward away from the center of the cam. Each lifting leg 42 moves linearly in the direction of rail 98. Proximity sensor 93 is mounted to the assembly and senses when the cam 64 is in the initial or home position.

Referring briefly to FIG. 7, the lower leg 42 includes the lifting foot 44 at the lower end. FIG. 8 is an exploded view of the lifting foot 44 on one of the legs 42. The lifting foot 44 includes an upstanding wall 102 that extends around a vertical corner preferably at about 90°. A lifting step 104 extends substantially horizontally from a lower portion of the upstanding wall 102 and also extends around the corner. The lifting feet 44 are designed to place the lifting shelf underneath the bottom surface of the respective corner of the tube storage rack or plate being lifted with the upstanding sidewalls 102 snug against the corner. With the lifting steps 104 at each of the four lifting feet 44 underneath the appropriate corner of the rack or plate being lifted, the rack robot in its entirety is lifted to lift the rack or plate by the shelves 104. As mentioned previously, it is desirable to lift the racks or plates from the bottom surface rather than grabbing the racks or plates with significant side force. The sidewall of the lifting foot 44 also includes an arched opening 106 that provides optical clearance to the corner of the rack or plate, and in particular the sidewall at the corner along the longer edge of an SBS formatted tube plate or rack, which is the standard location of an A1 notch on many SBS formatted tube racks or plates. The opening 106 allows optical detection of the location of the A1 notch without the need to set the rack or plate down, and release and clear the feet 44 from the respective corners.

Referring again to FIG. 7, the cam follower 94 is attached to or integral with a cam support member 108. The bearing rail 100 is attached to an upper leg member 110 with screws as shown. The upper leg member 110 is coupled to a strain gauge mounting block 112, and the cam follower support member 108 is attached to the strain gauge mounting block 112 with a screw as shown. An X-Y strain gauge is located on a horizontal surface of the strain gauge mounting block 112 (strain gauge not shown) and a Z-axis strain gauge is also located on the horizontal surface of the strain gauge mounting block 112 (strain gauge not shown). The lower leg member 42 includes a flange 114 that is mounted to the lower end of the strain gauge mounting block 112 with the screw as shown. A travel stop 116 is press fit into an opening on the top edge of the lower leg member 42, and serves as a physical stop in the event that there is excessive deflection of the strain gauge mounting block 112. FIG. 7 also shows a circuit board for the strain gauges, see reference number 118. The circuit board 118 is attached to the strain gauge mounting block with the screws as shown and receives wiring from the strain gauges.

Figure 5:
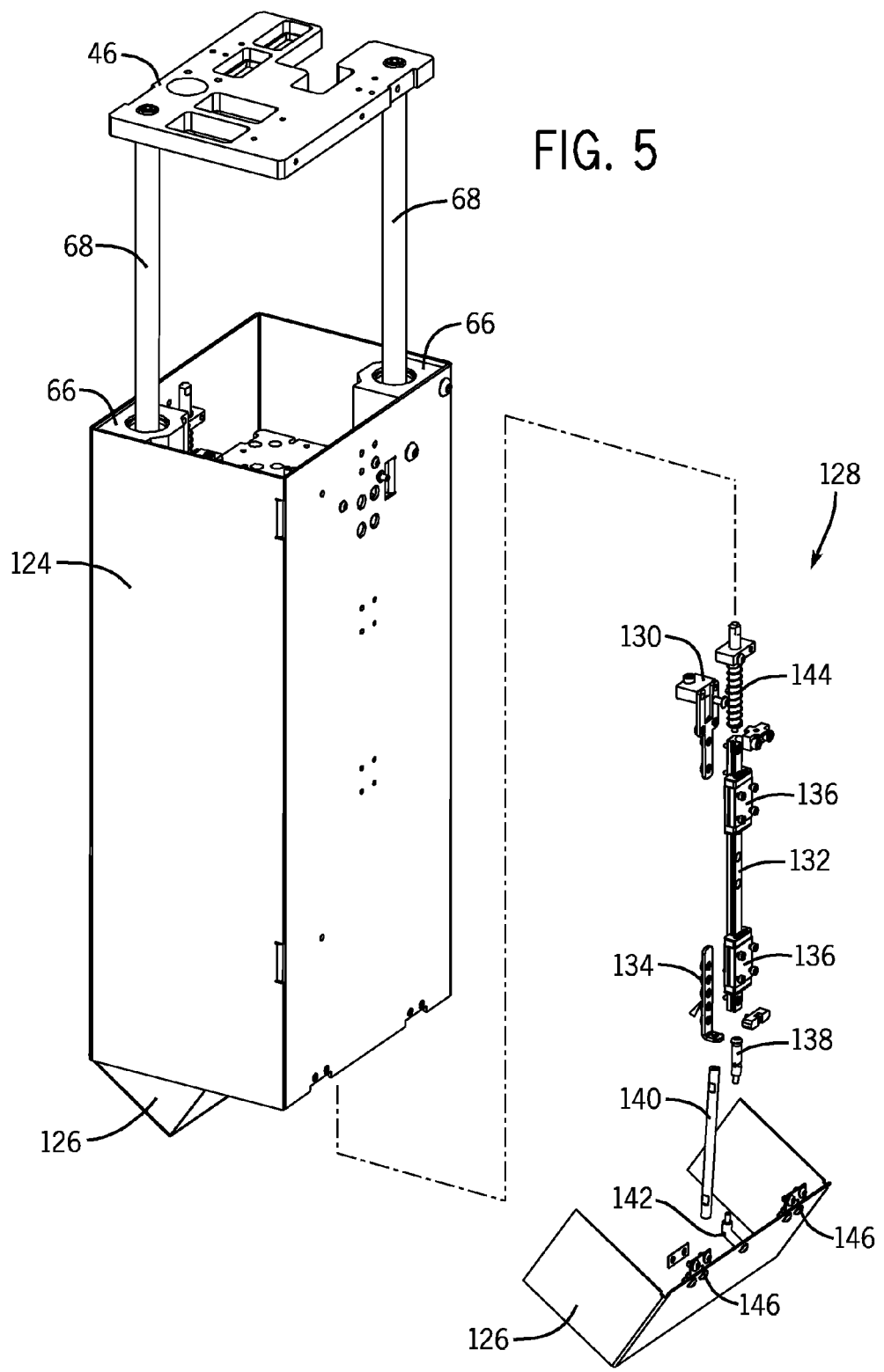
FIG. 5 is a partial assembly view illustrating bottom doors for the cover assembly as well as a mechanical coupling means to automatically open and close the doors during operation of the system.

Referring again to FIG. 4, the cover assembly 52 includes a magnetic drive rod 120 and a linear drive motor 122 mounted to the upper base plate 58. The drive rod 120 is mounted to a rectangular tubular sidewall cover 124. The motor 122 moves the rod 120 to move the sidewall cover 124 vertically with respect to the base. The cover assembly shown in FIG. 4 also includes a pair of bottom doors 126 that are pivotally mounted to the bottom of the sidewall cover 124. It should be noted again that the sidewall cover 124 can be used without the bottom doors 126 if desired. Referring now to FIG. 5, the tubular sidewall cover 124 is mounted to bearing blocks 66 which in turn are slidably mounted to rods 68 connected between the upper and lower base plates 58, 56, thus allowing for the cover 124 to moved vertically with respect to the base plates. FIG. 5 also shows a mechanical coupling assembly 128 for automatically closing the bottom door 126 when the rack robot is lifted after a tube rack or plate has been grabbed and lifted. Although FIG. 5 does not show a second coupling mechanism 128 exploded away on the other side, it should be understood that an identical or substantially similar mechanism is used to automatically open and close the bottom door 126 on the other side of the cover. The coupling mechanism 128 includes an end stop 130. A bearing rail 132 is attached to the end stop 130 at its top end, and is mounted to bracket 134 at its lower end. The rail 132 is mounted with bearing mounts 136 to the sidewall cover 124. The end stop 130 as well as the rail 132 and the bracket 134 move vertically relative to the sidewall cover 124 when the cover 124 moves vertically with respect to the base plate 56. The bracket 134 is mounted with a connector pin 138 to rod 140 which in turn is mounted to mounting finger 142 on the door 126. A spring mechanism 144 is mounted to the sidewall 124 so that the spring is compressed when the door is closed. The spring mechanism 144 therefore tends to force the bottom cover open when the base assembly 46 for the rack robot is lowered relative to the cover 124. The doors 126 are attached to the bottom of the sidewall 124 with hinges 146 and push open when the base assembly 46 is lowered relative to the cover 124, and close when the base 46 is raised relative to the cover 124. The operation of the motors 122 driving the vertical motion of the cover 124 and the Z-axis gantry motor raising and lowering the rack robot and base assembly 46 are coordinated in order to open and/or close the bottom doors 126 at the appropriate time.

Figure 9:
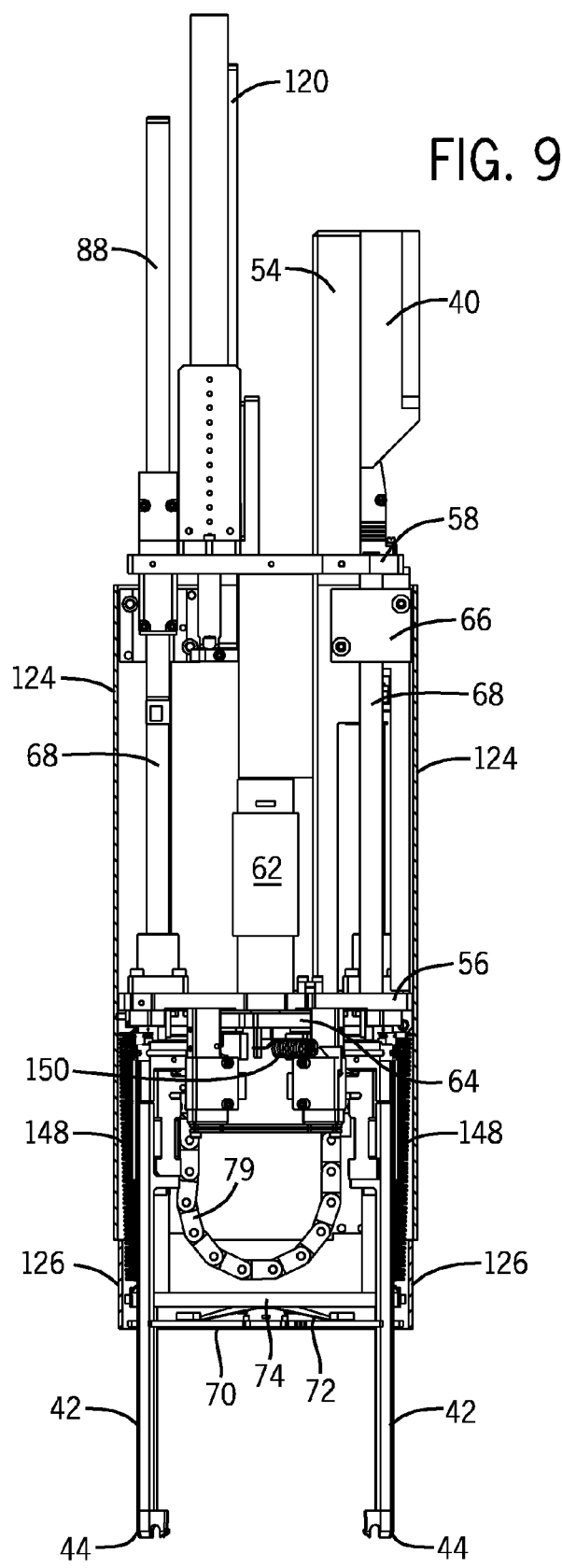
FIG. 9 is a longitudinal sectional view showing the rack robot constructed in accordance with the preferred embodiment of the invention in full assembly.

FIG. 9 is an elevation view showing the various components assembled with the side cover 124 and bottom doors 126 raised relative to the lifting feet 44. FIG. 9 shows springs 148 connected to the support beam 74 for the lid 70 as well as spring 150 connected to the cam 164 for biasing the cam in the home position.

Figure 10:
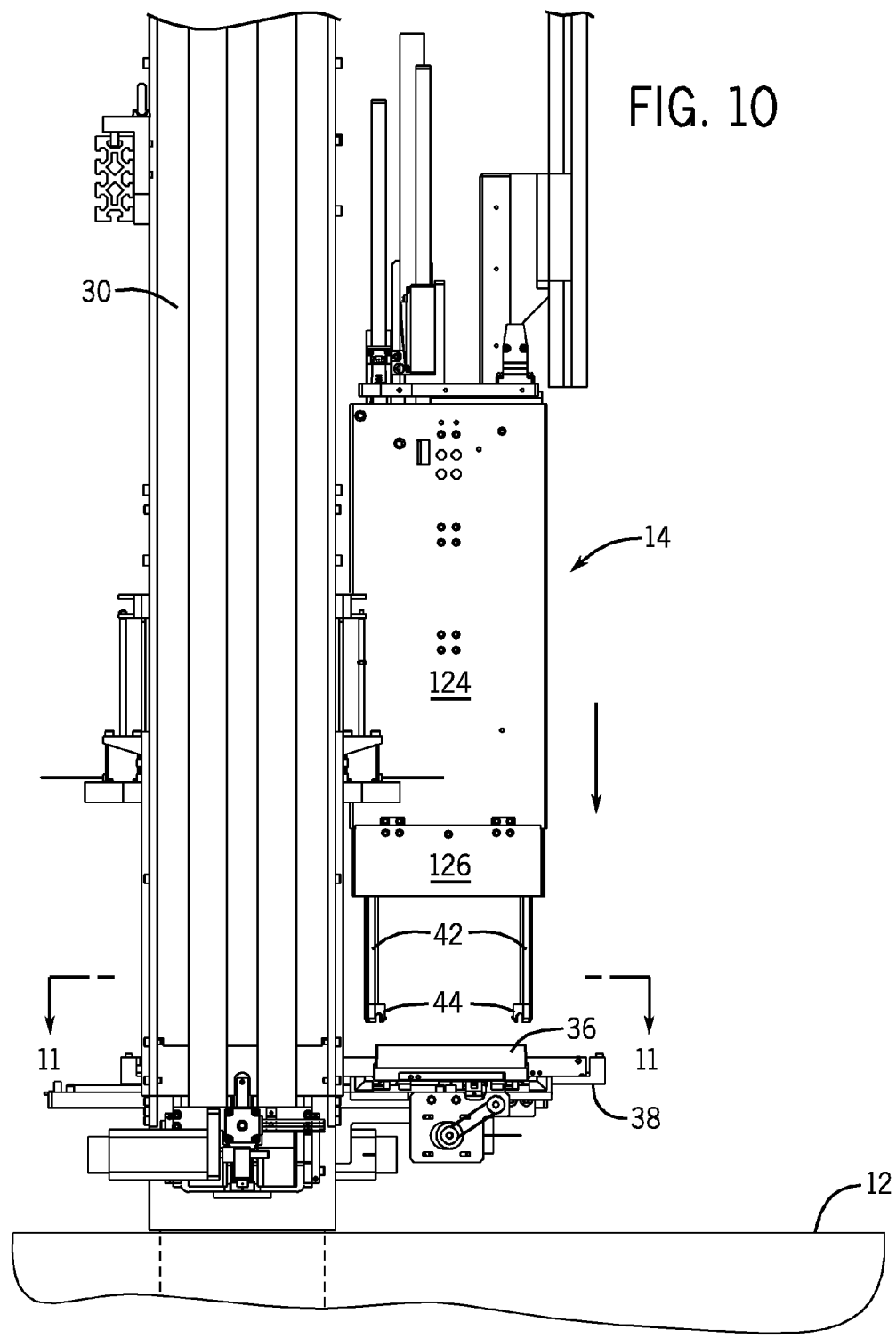
FIG. 10 is a view illustrating the rack robot being positioned to hover above a sample tube rack that has been presented outside of the cassette puller.
Figure 11:
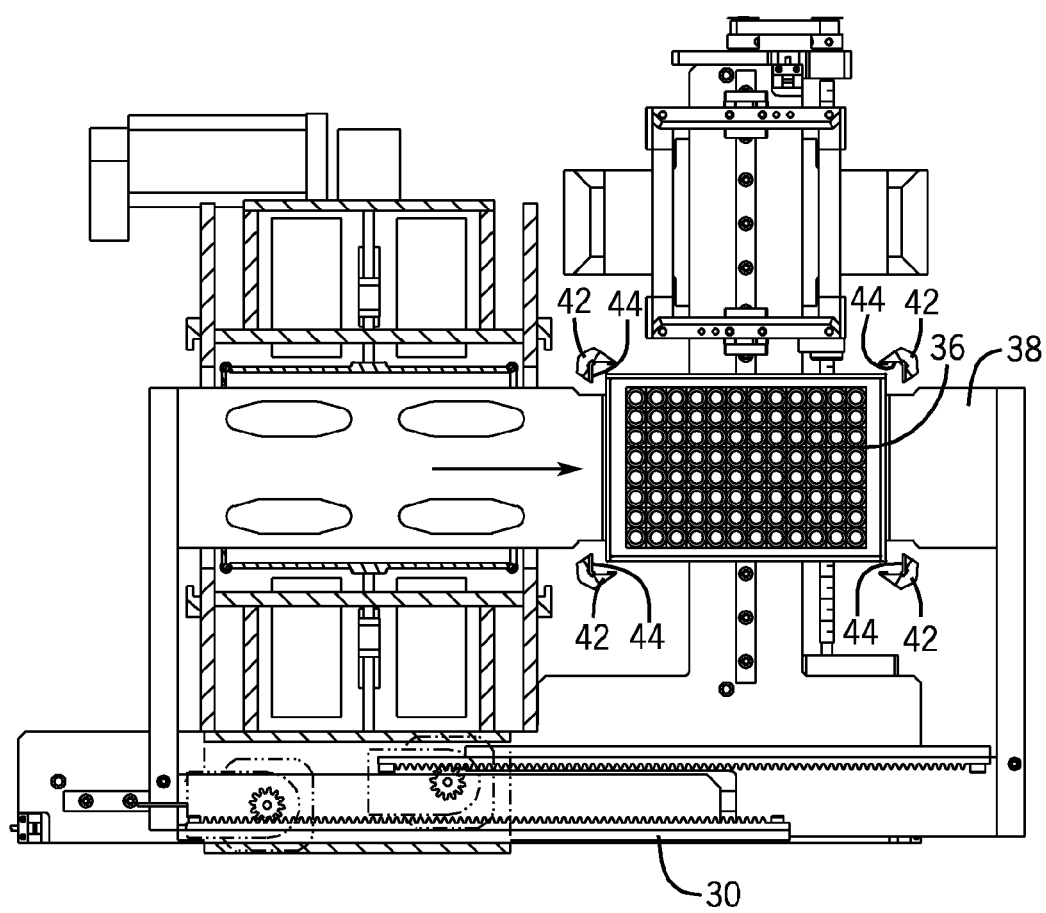
FIG. 11 is a view taken along line 11-11 in FIG. 10 illustrating a presented tube rack from the perspective of the rack robot.

FIG. 10 is a view similar to FIG. 2 showing the rack robot 14 being lowered and hovering above a tube storage rack 36 on an ejector plate 38 for the cassette puller 30. FIG. 11 is a downwardly looking sectional view taken along line 11-11 in FIG. 10, and illustrates the legs 42 and the lifting feet 44 being spread apart to provide clearance between the legs 42 and feet 44 for the corners of the tube rack 36 as the rack robot 14 is lowered. A rack robot constructed in accordance with the preferred embodiment of the invention as shown in the above described drawings is capable of promptly grabbing or lifting a rack or plate, for example within 0.3 seconds once the rack legs 42 and lifting feet 44 are lowered into the proper location. It is also capable of ensuring that storage tubes in the storage tube rack stay in place during lifting and transferring. In this regard, it takes about 0.5 seconds to properly place the lid above the tube storage rack 36. In addition, the lid 72 with the acceleration sensor can be used to sense tube height and determine whether one or more tubes are not properly seated in the tube rack 36, or as mentioned whether a tube cap is loose, or to identify labware height. Further, the rack robot 14 is designed so that the lifting legs and feet 44 can fit into narrow locations at or near the corners of the setting locations for the tube storage racks or plates. Often the setting location will be located in an ultra-low temperature environment, such as a −80° C. cache position in a tube picking mechanism 32 or the lower picking chamber in the tube picking mechanism 32. While the lifting legs 42 and feet 44 as well as the lid 72 (and the acceleration sensor) extend downward into the ultra-low temperature environment, electronic motors and electronic devices in general remain in the −20° C. environment, which improves the reliability of these components.

Figure 16:
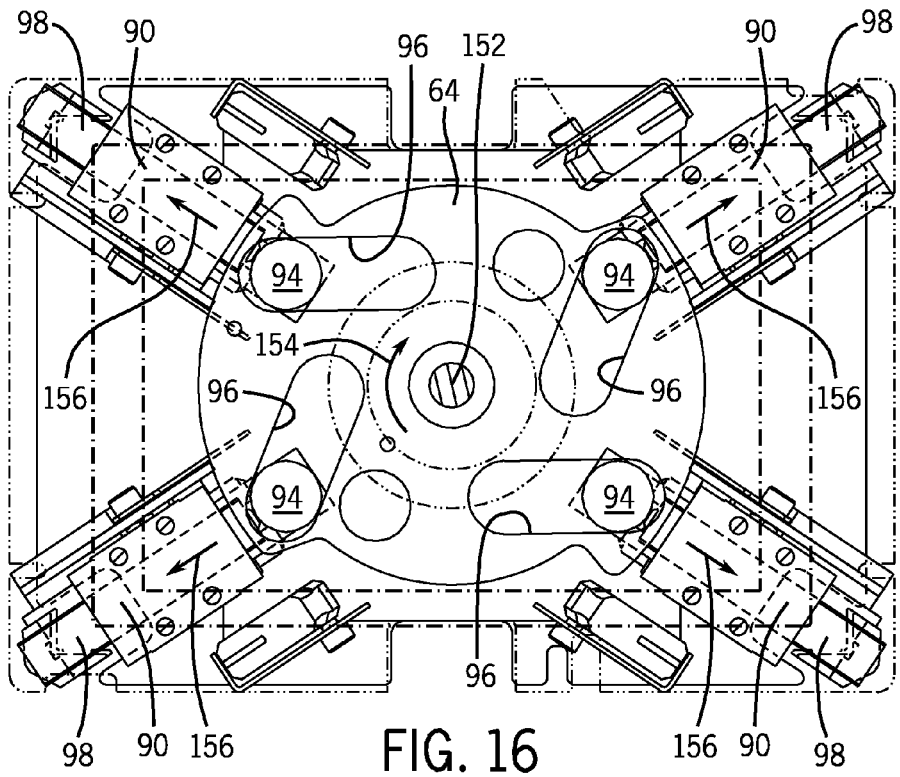
FIG. 16 is a schematic drawing taken along line 16-16 in FIG. 14 illustrating the position of the cam mechanism when the lifting legs and feet are spread apart prior to positioning the feet for lifting the sample tube rack.
Figure 17:
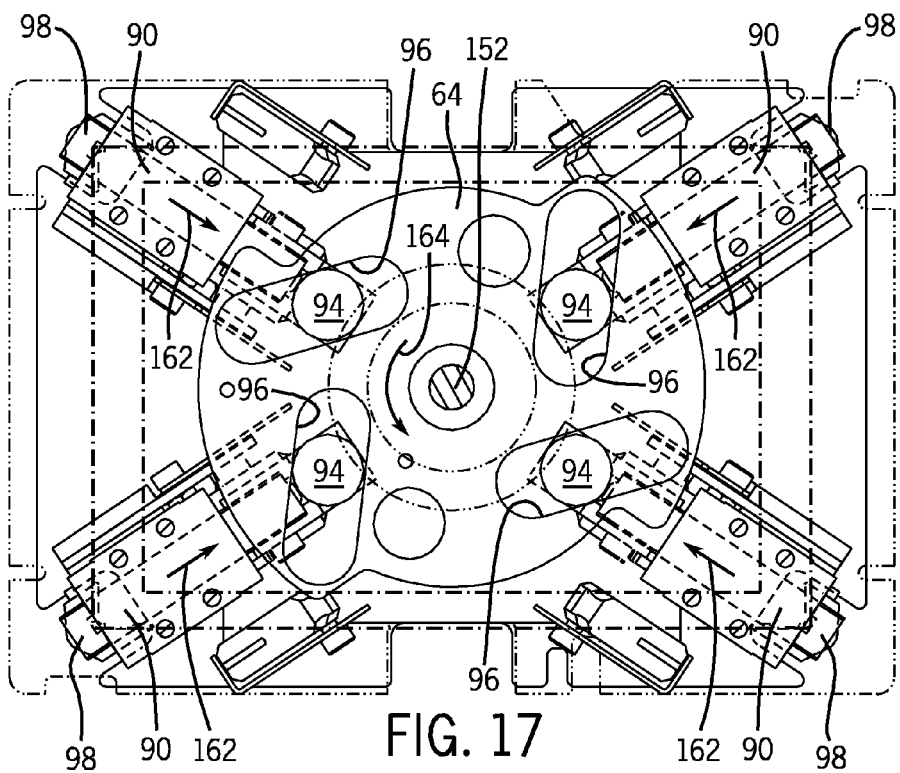
FIG. 17 is a similar view but taken along line 17-17 in FIG. 15 illustrating the position of the cam mechanism once the legs and feet are closed for lifting the rack.
Figure 20:
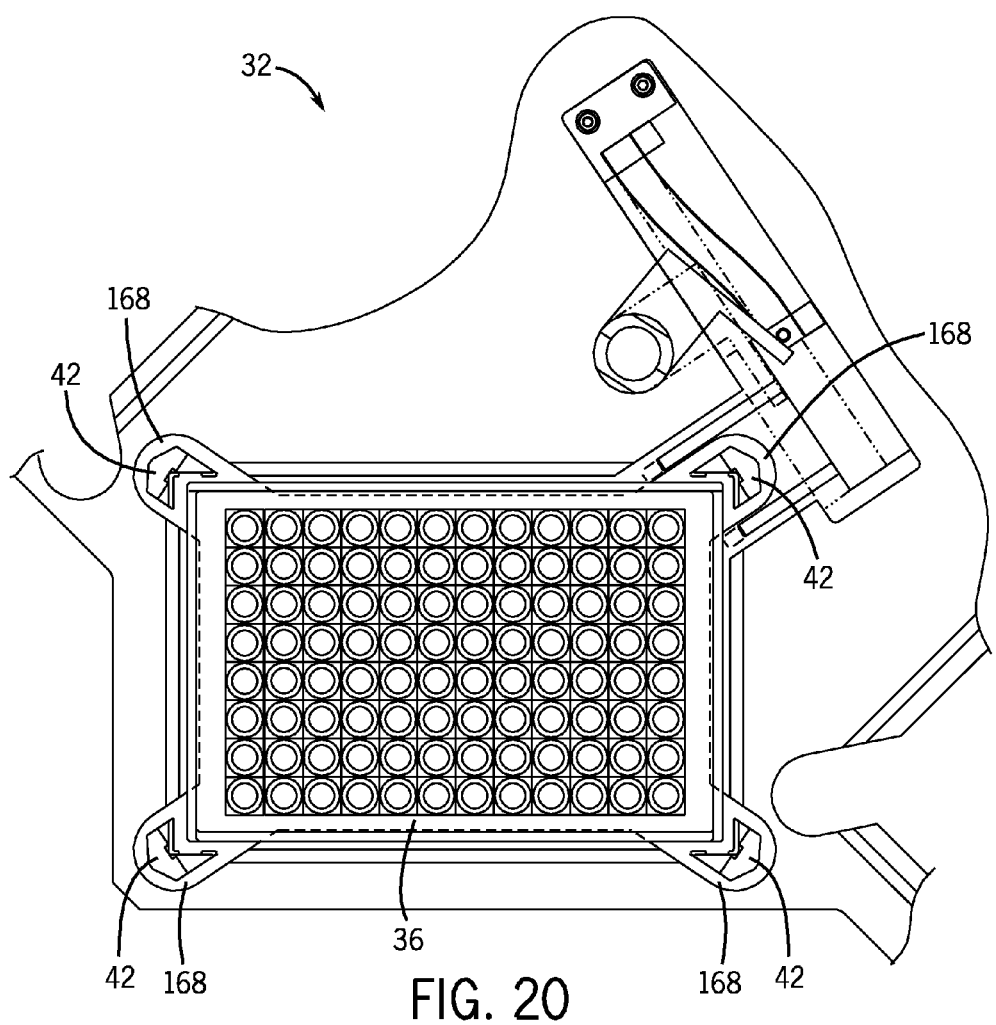
FIG. 20 is a top plan view showing the sample tube rack being set into a tube picking module with the rack robot.

FIGS. 12-19 schematically illustrate the rack robot lifting and transferring a tube storage rack 36. In FIG. 12, the rack robot 14 is positioned vertically above the tube storage rack 36. The gantry drive which includes the Z-axis indexing drive rail 22 is used to properly position the rack robot 14 in the appropriate position hovering above the tube storage rack 36 located in a first location, such as location 38 on the ejector plate for the cassette puller. In FIG. 12, the lid 72 is in its retracted or fully up position. FIG. 13 illustrates the next step in the process in which the lid 72 is lowered to an appropriate height as indicated by arrow 158. Rod 88 for the lid subassembly is driven downward by linear motor 86 in order to lower the lid 72 to the appropriate height. FIG. 14 shows the entire rack robot 14 being lowered in the direction illustrated by arrow 160 so that the lifting feet 44 are lowered to the appropriate height surrounding the corners of the tube storage rack 36 prior to closing the feet 44 for lifting. The rack robot 14 is lowered by the Z-axis gantry indexing drive motor (22A, FIG. 1). Note that the lid 72 is repositioned as it moves with the rack robot 14 to hover above the expected location of the storage tubes in the tube storage rack 36. If one or more tubes are not properly seated in the tube storage rack 36 or if the height of the storage tubes is higher than expected, the acceleration sensor on the lid 72 will provide a signal to the system control. Referring to FIG. 16, at this stage of operation the cam 64 is rotated to the fully open position as indicated by arrow 154 which in turn locates the cam followers 94 on the lifting legs 42 to the fully out position illustrated by arrows 156. It should be noted that the lifting legs move linearly inward and outward as the rails 98 pass linearly through the bearing brackets 90 and the path of the rails and cam followers 94 is either linearly towards a geometric center 152 or away from the geometric center 152. It is desired that the tube storage rack be aligned when lifted so that the geometric center of the tube storage rack aligns with the center point 152 of the cam mechanism; however, as described earlier the deflection of the lifting legs 42 can account for small positioning differences. FIGS. 15 and 17 illustrate the next step in the operation of the rack robot 14. In FIGS. 15 and 17, the cam 64 is rotated in the direction of 164 to move the lifting legs 42 and feet 44 inward according to arrows 162 so that the lifting feet 44 are positioned for a snug fit at each respective corner prior to lifting and transferring the tube storage rack 36. Signals from strain gauge sensors 166 on the upper lifting leg 42 provide feedback to the control system that are desirably used to adjust the operation of the cam actuator 62 to improve the quality of the grip on the tube storage rack. FIG. 18 illustrates the rack robot 14 in its entirety being lifted along with the tube storage rack 36, see arrow 168. The rack robot 14 is lifted by the Z-axis gantry indexing motor 22A, FIG. 1. Note that in FIG. 18 the cover 124 remains in the up position and bottom doors 126 remain open. In this position, the tube storage rack 36 is exposed, and barcode labels on the side of the tube storage rack 36 or on the bottom of the tubes can be read with a suitable barcode reader. Also, an optical sensor can be used to confirm or determine which corner of the tube rack 36 is near the A1 location in the tube rack. FIG. 19 illustrates the cover 124 being lowered in accordance with arrow 170. Cover drive rod 120 is driven by motor 122 to raise and lower the cover 124. Note that FIG. 19 shows the cover 124 being lowered enough so that the doors 126 extend downward while open to surround the tube storage rack 36. If the cover 124 were further lowered relative to the rack robot 14, the doors would automatically close to form a closed bottom as described above in connection with FIG. 5. The operation of the system to place the tube storage rack 36 in the same or another location is essentially the reverse operation described in FIGS. 12-19. For example, it will be necessary to raise the cover 124 and open the bottom doors 126, and in many cases continue raising the cover 124 to provide clearance when setting the tube storage rack 36 in a second location. FIG. 20 illustrates a tube storage rack 36 being set into a location in an ultra-low temperature chamber in a tube picking mechanism 32. Note that clearance 168 is provided at each corner of the setting location. FIG. 20 illustrates the lifting arms 42 and feet having set the tube storage rack 36 in the appropriate location such that cam 64 has been rotated to retract the legs 42 and feet away from the corners of the tube rack prior to lifting the rack robot 14.

FIG. 21 contains experimental data regarding experiments for temperature rise of samples with a 15 second exposure in a −20° C. environment. The purpose of the experiment was to determine whether a side cover and bottom doors on the rack robot are helpful to reduce temperature rise of samples during exposure to −20° C. environment. In conducting the experiment, a rack was equipped with thermocouples in defined positions and stored in an ultra-low temperature (−80° C.) freezer. The rack without a cover was then exposed to −20° C. warm air for 15 seconds. The data represented by the solid diamonds in FIG. 21 shows the average temperature rise with no cover and the open diamonds pertain to the maximum temperature rise with no cover. The experiment was run also with the use of a side cover and with the use of a side cover and a bottom cover. The solid squares show the average temperature rise with the side cover and the open squares show the maximum temperature rise with the side cover, whereas the solid triangles show the average temperature rise with both the side cover and bottom cover and the open triangles show the maximum temperature rise with the side cover and bottom cover. The data illustrates that use of the side cover reduces the warm up about 46%, and in addition to that, the use of a bottom cover can reduce the warm up an additional 11%.

In the foregoing description, certain terms have been used for brevity, clearness, and understanding. No unnecessary limitations are to be inferred therefrom beyond the requirement of the prior art because such terms are used for descriptive purposes and are intended to be broadly construed. The different configurations, systems, and method steps described herein may be used alone or in combination with other configurations, systems and method steps. It is to be expected that various equivalents, alternatives and modifications are possible within the scope of the appended claims.

What is claimed is:

1. An automated storage and retrieval system for storing sample tube racks or plates at an ultra-low or cryogenic temperature, the system comprising:
    a refrigerated enclosure maintained at a low temperature of approximately −15° C. to −30° C.;
    a first robot that moves a rack robot horizontally and vertically through the low temperature environment within the refrigerated enclosure; wherein the rack robot transports tube storage racks or plates through the low temperature environment within the refrigerated enclosure;
    at least one freezer located within the refrigerated enclosure, each freezer having at least one freezer bay maintained at or below −65° C. under normal operating conditions; wherein samples held in the tube storage racks or plates are stored in the at least one freezer bay maintained at or below −65° C.; and
    wherein said rack robot comprises:
    a vertically and horizontally repositionable base subassembly mounted to the first robot for moving the rack robot horizontally and vertically through the low temperature environment within the refrigerated enclosure;
    a lift subassembly mounted to the base subassembly and including a plurality of downwardly extending legs with lifting feet at the bottom end of each leg adapted to lift and hold a tube rack or plate being lifted and transported by the robot; and
    a tubular sidewall cover slidably mounted to the base subassembly and surrounding, the downwardly extending legs of the lift subassembly, said cover being repositionable vertically with respect to the base subassembly and with respect to the legs and lifting feet.

2. An automated storage and retrieval system for storing sample tube racks or plates as recited in claim 1 wherein the tubular sidewall cover comprises a rectangular tube.

3. An automated storage and retrieval system for storing sample tube racks or plates as recited in claim 1 further comprising one or more bottom doors that close underneath the lifting feet when a sample tube rack or plate is being lifted and transferred.

4. An automated storage and retrieval system for storing sample tube racks or plates as recited in claim 3 wherein the one or more doors are mechanically coupled to the tubular sidewall cover such that the one or more doors close automatically when the tubular sidewall cover is raised vertically relative to the lifting feet.

5. An automated storage and retrieval system for storing sample tube racks or plates as recited in claim 1 wherein the first robot is a gantry robot that moves the rack robot horizontally and vertically through the low temperature environment within the refrigerated enclosure.

6. An automated storage and retrieval system for storing sample tube racks or plates as recited in claim 1 further comprising a vertically repositionable lid that is capable of being positioned above the tube rack or plate located in closed lifting, fingers when the tube rack or plate is being lifted and transferred.

7. An automated storage and retrieval system for storing sample tube racks or plates as recited in claim 5 Wherein the relative height of the lid with respect to the lifting feet is adjustable.

8. An automated storage and retrieval system for storing sample tube racks or plates as recited in claim 5 further comprising, an acceleration sensor that outputs a signal in response to the acceleration of the lid and the system uses a signal from the acceleration sensor to determine whether one or more sample tubes are not properly seated within the tube rack.

9. An automated storage and retrieval system for storing sample tube racks or plates as recited in claim 5 further comprising a deflection sensor associated with the vertical movement of each leg and wherein the system uses a signal from the deflection sensor to determine whether an unexpected obstacle is present.

\* \* \* \* \*